(12) United States Patent
Sivaraman

(10) Patent No.: US 7,316,151 B2
(45) Date of Patent: Jan. 8, 2008

(54) APPARATUS AND METHOD FOR ACCURATE, REAL-TIME MEASUREMENT OF PIPELINE GAS

(75) Inventor: Alwarappa Sivaraman, Sugarland, TX (US)

(73) Assignee: Gas Technology Institute, Des Plaines, IL (US)

( * ) Notice: Subject to any disclaimer, the term of this patent is extended or adjusted under 35 U.S.C. 154(b) by 100 days.

(21) Appl. No.: 11/412,212

(22) Filed: Apr. 26, 2006

(65) Prior Publication Data

US 2007/0251298 A1    Nov. 1, 2007

(51) Int. Cl.
  *G01N 9/36*  (2006.01)
  *G01N 23/00*  (2006.01)
(52) U.S. Cl. .................... 73/24.05; 73/24.02
(58) Field of Classification Search .............. 73/23.31, 73/24.02, 24.05, 24.06, 32 A
  See application file for complete search history.

(56) References Cited

U.S. PATENT DOCUMENTS

| | | | |
|---|---|---|---|
| 3,381,265 A * | 4/1968 | Flook, Jr. ................... | 367/150 |
| 5,012,432 A | 4/1991 | Stetter et al. | |
| 5,494,826 A | 2/1996 | Stetter et al. | |
| 5,822,058 A | 10/1998 | Adler-Golden et al. | |
| 5,904,292 A | 5/1999 | McIntosh | |
| 6,116,080 A * | 9/2000 | Logue et al. .............. | 73/24.05 |

OTHER PUBLICATIONS

Web document: Hazelden et al., "Development and Deployment of an acoustic resonance technoogy for energy content measurement," http://research.nigc.ir/files/WGC/paper/add10666.pdf, 9 pages.*
Liss, W.E. et al., "Variability of Natural Gas Composition in Select Major Metropolitan Areas of the United States", Gas Research Institute, Mar. 1992.

* cited by examiner

*Primary Examiner*—Hezron Williams
*Assistant Examiner*—John Fitzgerald
(74) *Attorney, Agent, or Firm*—Mark E. Fejer

(57) ABSTRACT

An apparatus for BTU measurement of natural gas having at least one reference spherical acoustic resonator containing a reference gas, a sample gas spherical acoustic resonator containing a natural gas sample, a first acoustic transmitter adapted to transmit a first acoustic signal into the natural gas sample, a second acoustic transmitter adapted to transmit a second acoustic signal into the reference gas, a first acoustic receiver adapted to receive at least a portion of the first acoustic signal, and a second acoustic receiver adapted to receive at least a portion of the second acoustic signal. Using the third radial resonance frequencies for the sample gas and reference gas, a data processor operably connected with a signal output of the first acoustic receiver determines the specific gravity of the natural gas sample. The discovered linear relationship between specific gravity and heating value of natural gas enables a determination of the heating value from the measured specific gravity.

29 Claims, 3 Drawing Sheets

APPARATUS AND METHOD FOR ACCURATE, REAL-TIME MEASUREMENT OF PIPELINE GAS

BACKGROUND OF THE INVENTION

1. Field of the Invention

This invention relates to a method and apparatus for determining the Btu value of fuel gases. More particularly, this invention relates to a method and apparatus for determining the BTU value of pipeline gas in real time.

2. Description of Related Art

Accurate measurement of the heating value, i.e. BTU content, of hydrocarbon fuel gases is an essential component of their efficient and cost-effective use in a wide variety of applications. The heating value of natural gas, which typically contains in the range of about 80% to nearly 100% by weight methane, generally varies between about 900 and 1300 BTU/ft$^3$ depending upon the composition of the natural gas. In addition to methane, natural gas may contain various amounts of other hydrocarbons, such as ethane, propane, butane and non-hydrocarbons, such as $CO_2$ and $N_2$. The presence of such other components, in addition to affecting the heating value of the natural gas, may also affect the applications in which it is used, particularly applications which are sensitive to heat input. Because the heating value of natural gas consumed is the basis upon which consumers are charged, accurate measurement of the heating value on a continuous basis is essential to ensuring that consumers are neither undercharged nor overcharged for the amount of natural gas consumed. In addition, accurate measurement of the heating value on a continuous basis is essential to ensuring delivery of a gas having a constant BTU content to the consumer. To meet these requirements, monitoring of the heating value is required during all aspects of transmission from the source, storage and distribution to the consumer.

Currently, gas chromatography, calorimetry, NMR and absorption spectroscopy are typically employed for this purpose. However, these methods typically employ bulky or expensive equipment and are less than ideal for in-situ measurements. Also used are gas sensors comprising a coil of a fine platinum wire coated with a catalyst to form a bead. During operation, the sensor is heated by passing a current through the platinum wire whereby, when a combustible gas contacts the hot catalyst on the bead surface, the hydrocarbon gas reacts to produce heat from which the heat content of the gas can be determined (See, for example, U.S. Pat. No. 5,012,432 and U.S. Pat. No. 5,494,826). However, at least some of these devices are susceptible to numerous sources of error such as the composition of the sample gas and the age and composition of the sensor being utilized.

One recently developed approach to BTU measurement is an inferential natural gas flow rate system, which is based on sonic speed measurements and a cross correlation method used to compare two reflected signals to yield their time delays in a manner independent of the reflector distance from the transducer. However, in many instances, tests on a low pressure loop yielded errors from 1 to 4% in the sonic speed measurements. Thus, there is a need for a device that is consistent, accurate to better than 1%, and reliable.

At the present time, the energy content or heating value of pipeline gas, i.e. natural gas, is measured only at gas custody transfer areas. Because pipelines run several hundred miles after the transfer custody points, the energy content could be different at the distribution networks. Thus, it is necessary that the energy content at these locations be measured. Accordingly, a device having the desired accuracy and consistency, which can be used in-situ, and which can provide real-time heating values is particularly desirable to large individual customers having distribution network applications and to large industrial consumers of pipeline gas.

SUMMARY OF THE INVENTION

Accordingly, it is one object of this invention to provide a method and apparatus for accurately measuring the heating value of hydrocarbon fuel gases.

It is another object of this invention to provide a method and apparatus for accurately measuring the heating value of natural gas.

It is another object of this invention to provide a method and apparatus for accurately and continuously measuring the heating value of natural gas.

It is yet a further object of this invention to provide a method and apparatus for accurately and continuously measuring the heating value of natural gas in-situ.

It is still another object of this invention to provide a method and apparatus for accurately and continuously measuring the heating value of natural gas in real time.

It is still a further object of this invention to provide an apparatus for accurately and continuously measuring the heating value of natural gas which is suitable for use in remote locations.

These and other objects of this invention are addressed by an apparatus for BTU measurement of pipeline gas (also referred to herein as natural gas) comprising at least one reference gas spherical acoustic resonator containing a reference gas and a sample gas spherical acoustic resonator containing a natural gas sample. The sample gas spherical acoustic resonator is substantially identical to the reference gas spherical acoustic resonator. The apparatus further comprises propagation means for propagating an acoustic signal through each of the reference gas and the natural gas sample, means for maintaining a constant temperature and a constant pressure inside each of the reference gas spherical acoustic resonator and the sample gas spherical acoustic resonator, radial frequency measurement means for measuring a third radial resonance frequency of the reference gas and the natural gas sample, and calculation means for calculating a BTU content of the natural gas sample. To enable operation in remote locations, the apparatus in accordance with one embodiment of this invention is provided with an alternate power supply, such as a battery or solar backup battery.

In accordance with the method of this invention, a first hollow spherical acoustic resonator is filled with a reference gas and a second hollow spherical acoustic resonator substantially identical to the first hollow spherical acoustic resonator is filled with a natural gas sample. Acoustic waves are propagated through each of the reference gas and the natural gas sample after which a radial mode resonance frequency is measured in each of the first hollow spherical acoustic resonator and the second hollow spherical acoustic resonator. Thereafter, the specific gravity of the natural gas sample is determined, based upon which the heating value of the natural gas sample is determined.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

The invention disclosed and claimed herein is based upon the discovery of a linear relationship between the specific gravity of natural gas and the heating value of natural gas. Accordingly, the method and apparatus of this invention provide a simple means by which the specific gravity of a natural gas sample can be determined from which the heating value, or BTU content, is readily determined.

Figure 1:
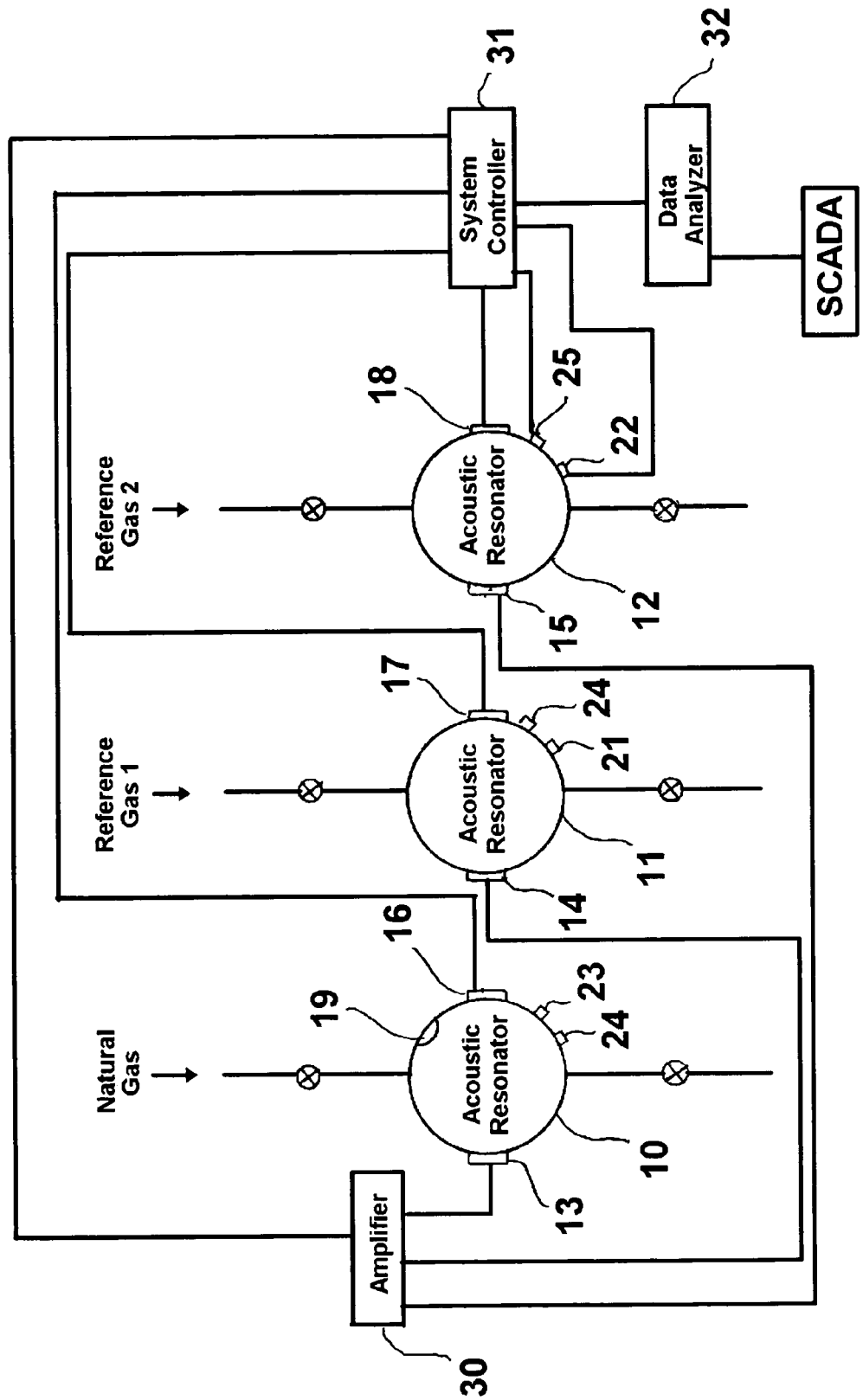
FIG. 1 is a schematic diagram of an apparatus for Btu measurement of pipeline gas in accordance with one embodiment of this invention.

FIG. 1 is a schematic diagram of a device for real-time BTU measurement of natural gas in accordance with one embodiment of this invention. As shown therein, the device comprises at least two, and preferably three, substantially identical spherical acoustic resonators, 10, 11, 12, one of which is filled with a natural gas sample and the others of which are filled with a reference gas. The reference gas mixture is selected based upon about 6800 gas analyses done from 26 major urban areas located in 19 states and each of the major geographical regions. A different reference gas mixture is required depending upon whether or not peak shaving is being employed. For determining the heating value of natural gas samples in which no peak shaving is being employed, the composition of the reference gas is 96.8 mol % $CH_4$, 0.5 mol % $C_2H_6$, 0.15 mol % $C_3H_8$, 0.10 mol % $n\text{-}C_4H_{10}$, 0.05 mol % $n\text{-}C_5H_{12}$, 1.2 mol % $CO_2$, and 1.2 mol % $N_2$. For determining the heating value of natural gas samples in which peak shaving is being employed, the composition of the reference gas is 73.0 mol % $CH_4$, 1.7 mol % $C_2H_6$, 12.9 mol % $C_3H_8$, 0.3 mol % $n\text{-}C_4H_{10}$, 0.1 mol % $n\text{-}C_6H_{14}$, 0.7 mol % $CO_2$, and 11.3 mol % $N_2$. In accordance with one embodiment of this invention, the reference gas mixtures are sealed in the reference gas spheres at a pressure of about 30 psia.

Attached to each spherical acoustic resonator is an acoustic signal transmitter 13, 14, 15, each of which is connected with an amplifier 30, through which a suitable acoustic signal is introduced into the corresponding spherical acoustic resonator. In accordance with one preferred embodiment of this invention, the frequencies of the acoustic signals introduced into the spherical acoustic resonators are less than about 50 kHz. The transmitters are excited by a sine wave of 5V peak to peak and acoustic waves are generated in the three spheres. The received signals at the receiver transducers of the spheres are amplified after being sent through a noise filter. The respective third radial resonance frequencies of distribution gas mixture filled in the sample sphere and reference standard mixture in the reference spheres are measured at the same temperature and pressure using a BTU control system 31. Accordingly, attached to each spherical acoustic resonator is a temperature sensor 20, 21, 22 and a pressure sensor 23, 24, 25. The BTU control system provides the excitation energy for the sender transducers to propagate acoustic waves in the spheres and amplifies the receiver signals from the receiver transducers amounted on all of the spheres. The control unit also locates the respective third radial resonance peaks by auto tuning or rapid sweeping method within a preset frequency window. Once the respective third radial resonance frequency peaks are found, they are locked on and tracked by a control program which also determines the BTU values in real time using the following equations and the specific gravity of the reference gas integrated in the same program of the automated system. The BTU values are displayed or sent to a SCADA system of the client's location at every set time interval of client's interest.

Also attached to each spherical acoustic resonator is an acoustic signal receiver 16, 17, 18 which is operably connected with the BTU system controller 31. In addition to controlling the acoustic signal input, the BTU system controller also receives the output signals from the acoustic signal receivers. Information from the BTU system controller is then transmitted to a data analyzer 32 in which the data is processed to provide the BTU content of the natural gas sample.

For a fluid confined in a sphere, the sonic velocity is related to its acoustic resonance frequency by the equation:

$$V = 2\pi a f_{30}/v_{30} \tag{1}$$

where V is the sonic velocity in meters per second, a is the radius of the sphere (e.g. 25 mm), $f_{30}$ is the frequency of the third radial mode and $V_{30}$ is the respective Eigen value (7.72525184) for the sphere.

In the following equations, $V_1$ is the velocity, $f^1$ is the third radial frequency, $\rho_1$ is the density of the sample gas mixture, and $V_r$ is the velocity, $f^r$ is the frequency, $\rho_r$ is the density for the reference standard gas mixture at the same pressure and temperature, respectively.

$$V_1 = 2\pi a f^1{}_{30}/v_{30} \tag{2}$$

$$V_r = 2\pi a f^r{}_{30}/v_{30} \tag{3}$$

$$(V_1{}^2/V_r{}^2) = (f^1/f^r)^2 \tag{4}$$

Velocity is related to density of gas by the following equations:

$$(V_1{}^2/V_r{}^2) = (\rho_r/\rho_1) \tag{5}$$

$$(\rho_1/\rho_r) = (f^r/f^1)^2 \tag{6}$$

Knowing $\rho_r$, $f^1$ and $f^r$ in equation (6), $\rho_1$ can be calculated.

$$\text{Specific gravity of gas mixture} = \rho_1/\rho_{air} \tag{7}$$

Figure 2:
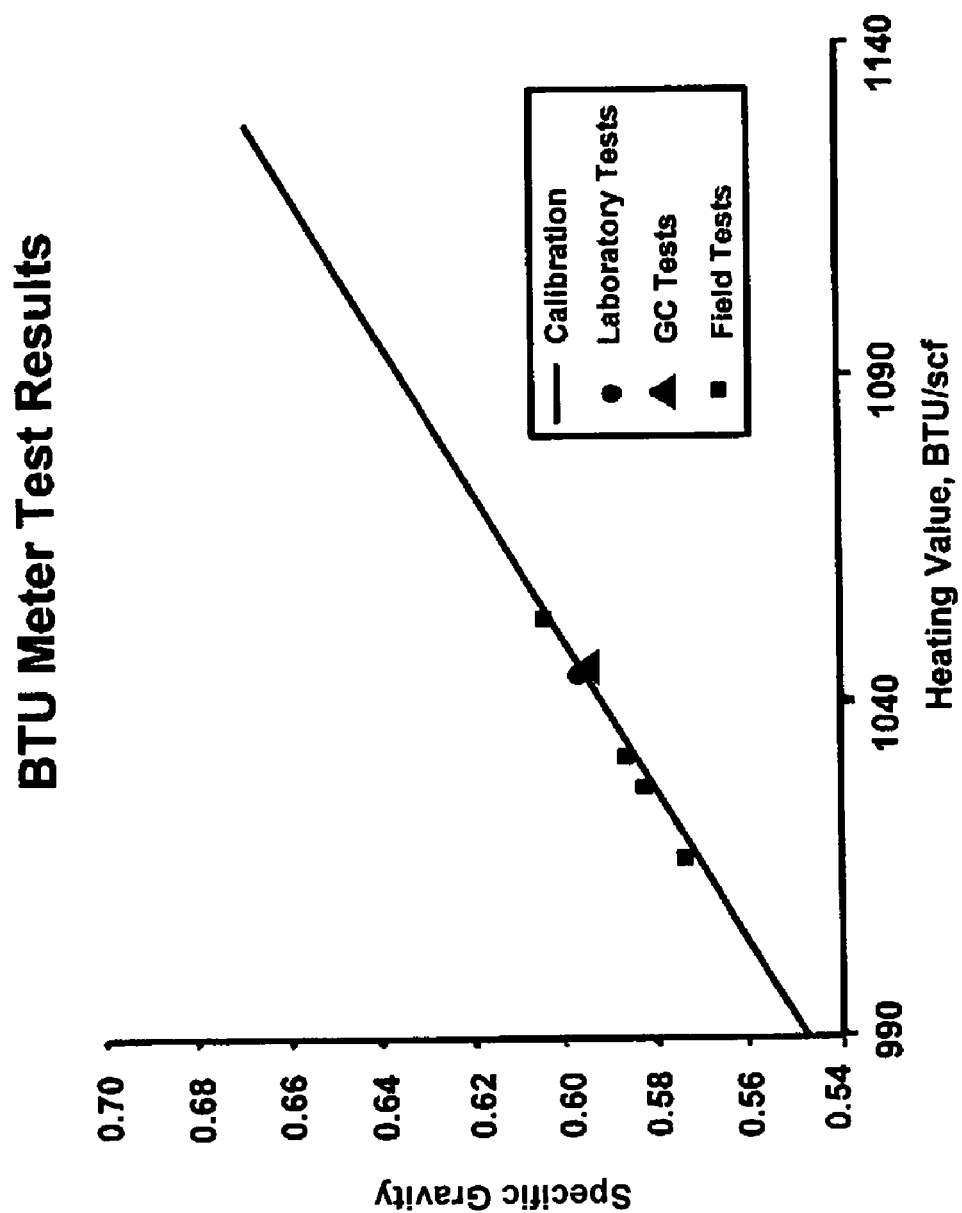
FIG. 2 is a diagram showing the relationship between the heating value and specific gravity of natural gas.

Wobbe Index=(Gross Calorific Value for gas mixture)/$\sqrt{\text{Specific gravity of mixture}}$ As previously indicated, it has been discovered that there is a linear relationship between the heating value and the specific gravity of a natural gas mixture as shown by the calibration curve in FIG. 2. From the measured respective third radial resonance frequencies, the specific gravity of the mixture can be determined from the equations (6) and (7) knowing the specific gravity of the reference gas mixture (0.5767). Now the heating value for the sample gas can be determined from the following relation:

$$\text{(Specific Gravity)} = (0.000878)(\text{Heating Value}) - 0.32185 \tag{8}$$

In addition to the calibration curve, the results of laboratory and field tests conducted at different locations (gas distribution and storage locations) in the United States are shown along with gas chromatography results in FIG. 2 for comparison and its performance.

The accuracy of measurements for the lab tests and limited field tests (at four different gas distribution sites) are within 0.3% compared to the gas chromatography calibration data. This device is suitable for use in the specific gravity range from 0.54 to 0.7 (with peak shaving the range is extended to 0.95) and the respective heating value range from 990 BTU to 1126 BTU (with peak shaving the range can be extended to 1225 BTU). Also, a new reference gas mixture sealed in the second reference sphere of the device can be used for a pipeline for propane/air (2.5-50 percent blend) peak shaving gas mixture used during peak demand mostly in the Northeast and Southeast regions of the United States.

An oxygen sensor in the sample sphere is used to monitor the nitrogen content ($N_2$ content (mol %)=3.71×oxygen content (mol %)) in the air mixed stream. The nitrogen content normally exceeds 2.0 mol % when propane air gas mix is distributed in some states during peak demand. Once higher nitrogen content is detected, the logic system of the BTU system controller will automatically switch to the second reference standard sphere containing propane air mix standard. A propane/air blend gas mixture (23 mol % blend in a nominal gas) of known specific gravity (0.7473) can be used as a reference. The procedure of determining the specific gravity of the peak shaving sample mixture from their respective radial resonance frequencies is the same as discussed above. The following equation can be used for these special gas mixtures to determine the heating value:

$$\text{Heating Value}=(563.5)(\text{Specific gravity})+682.66 \quad (9)$$

Figure 3:
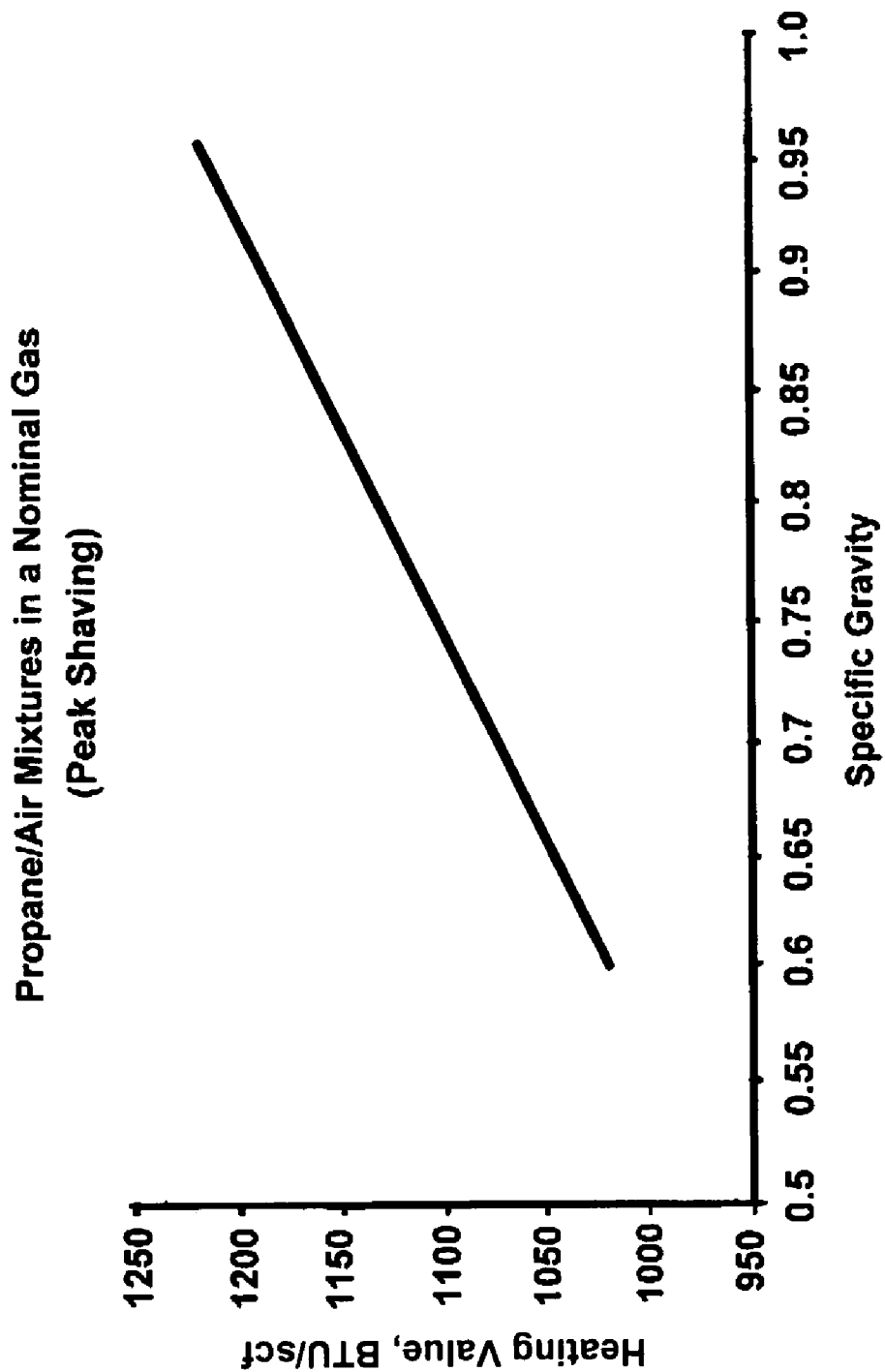
FIG. 3 is a diagram showing the relationship between heating value and specific gravity for natural gas in which peak shaving, i.e. the addition of propane/air mixtures to natural gas to boost the heating value, is employed.

The calibration curve for peak shaving propane air mix natural gas blend is shown in FIG. 3.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

What is claimed is:

1. An apparatus for BTU measurement of natural gas comprising:
    at least one reference spherical acoustic resonator containing a reference gas;
    a sample gas spherical acoustic resonator containing a natural gas sample;
    a first acoustic transmitter adapted to transmit a first acoustic signal into said natural gas sample;
    a second acoustic transmitter adapted to transmit a second acoustic signal into said reference gas;
    a first acoustic receiver adapted to receive at least a portion of said first acoustic signal;
    a second acoustic receiver adapted to receive at least a portion of said second acoustic signal;
    data processing means operably connected with a signal output of said first acoustic receiver for determining a specific gravity of said natural gas sample based upon said first acoustic signal received by said first acoustic receiver; and
    conversion means for converting said specific gravity of said natural gas sample to a BTU content of said natural gas sample.

2. An apparatus in accordance with claim 1 further comprising a second reference spherical acoustic resonator containing a second reference gas.

3. An apparatus in accordance with claim 2 further comprising switching means for switching transmission of said second acoustic signal between said first reference gas and said second reference gas.

4. An apparatus in accordance with claim 1 further comprising control means for controlling said BTU content of natural gas operably connected with said data processing means.

5. An apparatus in accordance with claim 4, wherein said control means comprises a SCADA system.

6. An apparatus in accordance with claim 1 further comprising nitrogen measurement means disposed in said sample gas spherical acoustic resonator for measuring a nitrogen content of said natural gas sample.

7. An apparatus in accordance with claim 6, wherein said nitrogen measurement means is an oxygen sensor.

8. A method for real-time measurement of BTU content of natural gas comprising:
    introducing a reference gas into a first hollow spherical acoustic resonator;
    introducing a natural gas sample into a second hollow spherical acoustic resonator substantially identical to said first hollow spherical acoustic resonator;
    transmitting a first acoustic signal through said natural gas sample;
    transmitting a second acoustic signal through said reference gas;
    measuring a third radial resonance frequency in each of said reference gas and said natural gas;
    determining a specific gravity of said natural gas sample; and
    determining said BTU content based upon said specific gravity.

9. A method in accordance with claim 8, wherein said reference gas and said natural gas are maintained at a substantially constant temperature and pressure.

10. A method in accordance with claim 8, wherein a frequency of said first acoustic signal and said second acoustic signal is less than about 50 kHz.

11. A method in accordance with claim 8 further comprising determining an oxygen content of said natural gas sample.

12. A method in accordance with claim 11, wherein said first acoustic signal is transmitted through a second reference gas in a third hollow spherical acoustic resonator upon determination of a threshold amount of oxygen in said natural gas sample.

13. An apparatus for BTU measurement of pipeline gas comprising:
    a reference gas sphere containing a reference gas;
    a sample gas sphere containing a pipeline gas sample;
    a sample gas sphere acoustic transmitter adapted to transmit an acoustic signal into said pipeline gas sample;
    a sample gas sphere acoustic receiver adapted to receive at least a portion of said acoustic signal exiting from said pipeline gas sample;
    a reference gas sphere acoustic transmitter adapted to transmit said acoustic signal into said reference gas disposed within said reference gas sphere;
    a reference gas sphere acoustic receiver adapted to receive at least a portion of said acoustic signal exiting from said reference gas;
    pressure means for maintaining a substantially constant pressure in said reference gas sphere and said sample gas sphere;

temperature means for maintaining a substantially constant temperature in said reference gas sphere and said sample gas sphere;

radial frequency measurement means for measuring a radial frequency of said reference gas and said pipeline gas sample; and data processing means for determining a specific gravity of said pipeline gas sample and converting said specific gravity to BTU content of said pipeline gas sample operably connected with a signal output of each of said sample gas sphere acoustic receiver and said reference gas sphere acoustic receiver.

14. An apparatus in accordance with claim 13, wherein said sample gas sphere acoustic receiver is disposed within a sample gas sphere wall of said sample gas sphere.

15. An apparatus in accordance with claim 13, wherein said sample gas sphere acoustic receiver is disposed within a sample gas sphere wall of said sample gas sphere.

16. An apparatus in accordance with claim 13, wherein said reference gas sphere acoustic transmitter is disposed within a reference gas sphere wall of said reference gas sphere.

17. An apparatus in accordance with claim 13, wherein said reference gas sphere receiver is disposed within a reference gas sphere wall of said reference gas sphere.

18. An apparatus in accordance with claim 13, wherein said sample gas sphere acoustic transmitter is aligned to generate at least one radial frequency.

19. An apparatus in accordance with claim 13, wherein said reference gas sphere transmitter is aligned to generate at least one radial frequency.

20. An apparatus in accordance with claim 13, wherein said sample gas sphere and said reference gas sphere have the same size.

21. An apparatus in accordance with claim 13, wherein said sample gas sphere and said reference gas sphere are substantially identical and have an internal diameter of about 2 inches.

22. An apparatus in accordance with claim 13, wherein said reference gas sphere transmitter and said sample gas sphere transmitter are suitable for propagating acoustic waves having frequencies one of less than and equal to about 50 kHz.

23. A method for determining a BTU content of a pipeline fuel gas comprising the steps of:

filling a first hollow spherical resonator with a reference gas;

filling a second hollow spherical resonator substantially identical to said first hollow spherical resonator with a sample gas;

propagating acoustic waves through each of said reference gas and said sample gas;

measuring a radial mode resonance frequency in each of said first hollow spherical resonator and said second hollow spherical resonator;

determining a specific gravity of each of said reference gas and said sample gas; and determining a BTU content of said sample gas based upon said specific gravity.

24. A method in accordance with claim 23, wherein said first hollow sphere resonator and said second hollow sphere resonator have a diameter of one of less than and equal to about 2 inches.

25. A method in accordance with claim 23, wherein said acoustic waves have frequencies one of less than and equal to about 50 kHz.

26. An apparatus for BTU measurement of pipeline gas comprising:

a reference gas spherical resonator containing a reference gas;

a sample gas spherical resonator containing a pipeline gas sample, said sample gas spherical resonator substantially identical to said reference gas spherical resonator;

propagation means for propagating an acoustic signal through each of said reference gas and said pipeline sample gas;

means for maintaining a constant temperature and a constant pressure inside each of said reference gas spherical resonator and said sample gas spherical resonator;

radial frequency measurement means for measuring a third radial resonance frequency of said reference gas and said pipeline gas sample; and calculation means for calculating a BTU content of said pipeline sample gas.

27. An apparatus in accordance with claim 26, wherein said propagation means is suitable for propagating acoustic waves having frequencies one of less than and equal to about 50 kHz.

28. An apparatus in accordance with claim 26, wherein said reference gas spherical resonator and said sample gas resonator are substantially equal in size.

29. An apparatus in accordance with claim 26, wherein said reference gas spherical resonator and said sample gas resonator have a diameter of one of less than and equal to about 2 inches.

* * * * *